US010376429B2

United States Patent
Hao et al.

(10) Patent No.: US 10,376,429 B2
(45) Date of Patent: Aug. 13, 2019

(54) THREE-DIMENSIONAL SHEET MATERIAL AND ABSORBENT ARTICLES INCLUDING SUCH MATERIAL

(71) Applicant: Kimberly-Clark Worldwide, Inc., Neenah, WI (US)

(72) Inventors: Xueen George Hao, Beijing (CN); Lin Miao, Beijing (CN); Chunlei Pu, Beijing (CN); Tongtong Zhang, Beijing (CN)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 770 days.

(21) Appl. No.: 15/053,476

(22) Filed: Feb. 25, 2016

(65) Prior Publication Data
US 2016/0175172 A1    Jun. 23, 2016

Related U.S. Application Data

(62) Division of application No. 14/362,612, filed as application No. PCT/CN2011/002177 on Dec. 23, 2011, now abandoned.

(51) Int. Cl.
| A61F 13/45 | (2006.01) |
| A61F 13/537 | (2006.01) |
| B32B 3/30 | (2006.01) |
| A61F 13/511 | (2006.01) |

(Continued)

(52) U.S. Cl.
CPC ........ *A61F 13/53713* (2013.01); *A61F 13/45* (2013.01); *B32B 3/30* (2013.01); *A61F 13/15731* (2013.01); *A61F 13/512* (2013.01); *A61F 13/51104* (2013.01); *A61F 2013/4587* (2013.01); *A61F 2013/53721* (2013.01); *A61F 2013/53782* (2013.01);

(Continued)

(58) Field of Classification Search
CPC .............. A61F 13/51104; A61F 13/512; A61F 13/53713; A61F 2013/4587; A61F 2013/53782; A61F 13/15731; A61F 2013/53721; B32B 3/30
See application file for complete search history.

(56) References Cited

U.S. PATENT DOCUMENTS

| 3,542,634 A | 11/1970 | Such et al. |
| 4,333,979 A | 6/1982 | Sciaraffa et al. |
| 4,704,112 A | 11/1987 | Suzuki et al. |

(Continued)

FOREIGN PATENT DOCUMENTS

| JP | 4255440 B2 | 4/2009 |
| KR | 10-2005-0053696 A | 6/2005 |
| WO | WO 9858795 | 12/1998 |

OTHER PUBLICATIONS

Search Report and Written Opinion for PCT/CN2011/002177, dated Oct. 4, 2012, 8 pages.

*Primary Examiner* — Peter S Vasat
(74) *Attorney, Agent, or Firm* — Kimberly-Clark Worldwide, Inc.

(57) ABSTRACT

The present application discloses and claims a three-dimensional sheet material and an absorbent article which utilizes the sheet material within the article. The three-dimensional sheet material is designed to minimize the contact area on one side of the material thereby making it useful for various applications including a body contacting top sheet or liner material.

14 Claims, 6 Drawing Sheets

(51) Int. Cl.
 *A61F 13/512* (2006.01)
 *A61F 13/15* (2006.01)

(52) U.S. Cl.
 CPC ... *B32B 2555/02* (2013.01); *Y10T 428/24273* (2015.01); *Y10T 428/24479* (2015.01)

(56) References Cited

U.S. PATENT DOCUMENTS

| | | | |
|---|---|---|---|
| 4,741,941 A * | 5/1988 | Englebert | A47L 13/16 15/209.1 |
| 4,761,322 A | 8/1988 | Raley | |
| 5,667,619 A | 9/1997 | Alikhan | |
| 5,667,625 A | 9/1997 | Alikhan | |
| 5,674,591 A | 10/1997 | James et al. | |
| 5,817,394 A | 10/1998 | Alikhan et al. | |
| 5,833,679 A | 11/1998 | Wada | |
| 5,895,380 A | 4/1999 | Turi et al. | |
| 5,997,986 A | 12/1999 | Turi et al. | |
| 6,090,089 A | 7/2000 | Tsuji et al. | |
| RE38,505 E | 4/2004 | James et al. | |
| 6,739,024 B1 | 5/2004 | Wagner | |
| 6,849,319 B2 | 2/2005 | Cree et al. | |
| 7,060,344 B2 | 6/2006 | Pourdeyhimi et al. | |
| 7,386,924 B2 | 6/2008 | Muth et al. | |
| 7,569,264 B2 | 8/2009 | Toyoshima et al. | |
| 2002/0099347 A1* | 7/2002 | Chen | A61F 13/512 604/369 |
| 2003/0203691 A1* | 10/2003 | Fenwick | B29C 59/022 442/327 |
| 2004/0116029 A1 | 6/2004 | Kelly et al. | |
| 2004/0127875 A1 | 7/2004 | Hammons et al. | |
| 2005/0003152 A1 | 1/2005 | Thomas et al. | |
| 2007/0029694 A1 | 2/2007 | Cree et al. | |
| 2008/0114317 A1* | 5/2008 | Seyler | A61F 13/53713 604/369 |
| 2008/0294135 A1* | 11/2008 | Hara | A61F 13/15203 604/367 |
| 2009/0011209 A1* | 1/2009 | Steinberger | C08G 18/664 428/219 |
| 2009/0299316 A1 | 12/2009 | Seyler | |
| 2010/0249740 A1 | 9/2010 | Miyamoto et al. | |
| 2012/0136329 A1 | 5/2012 | Carney | |

* cited by examiner

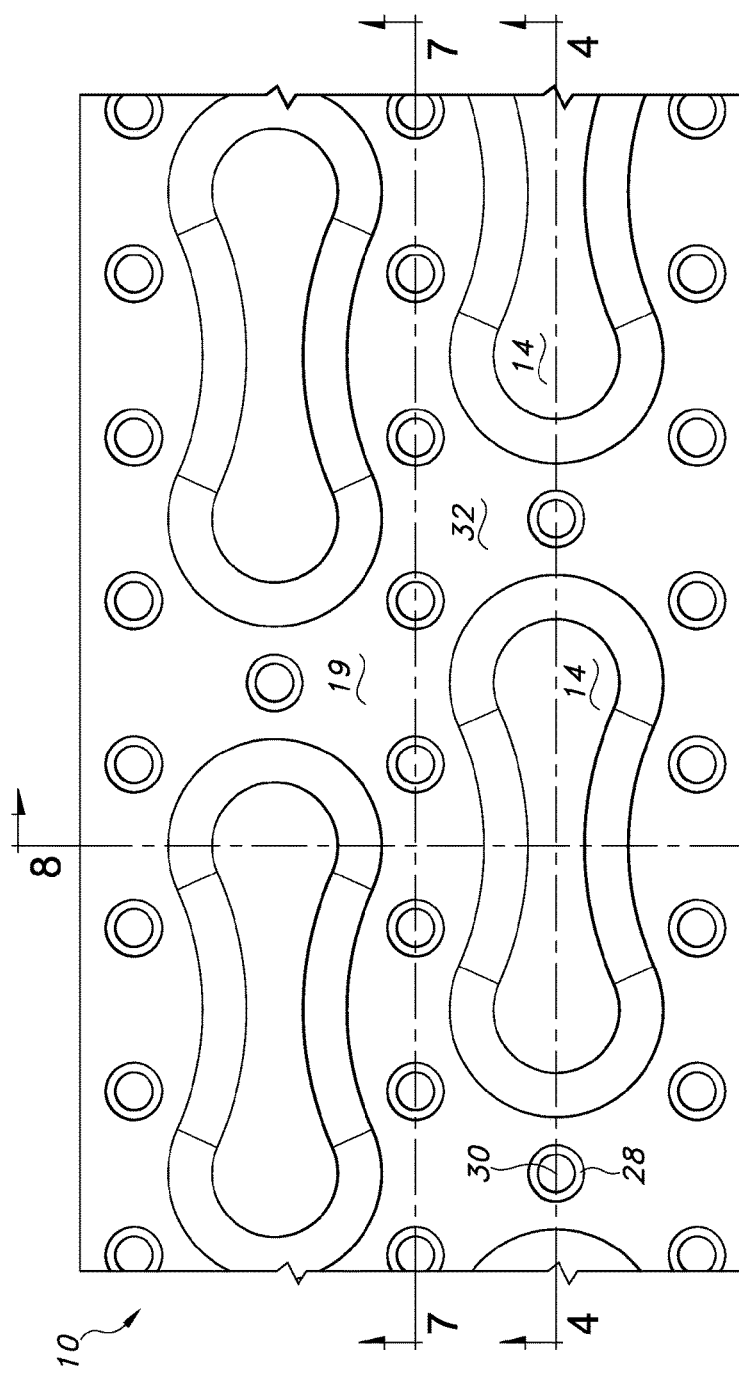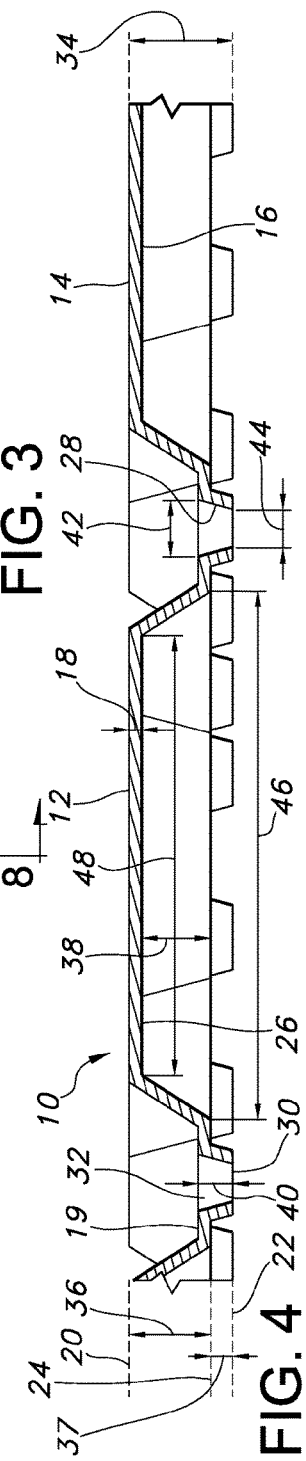

THREE-DIMENSIONAL SHEET MATERIAL AND ABSORBENT ARTICLES INCLUDING SUCH MATERIAL

CROSS REFERENCE TO RELATED APPLICATION

This application is a divisional of U.S. application Ser. No. 14/362,612 filed on Jun. 4, 2014, which is the national stage entry of International Patent Application No. PCT/CN2011/002177 having a filing date of Dec. 23, 2011, the entire contents of which are incorporated herein by reference.

BACKGROUND OF THE INVENTION

Absorbent articles such as diapers, training pants, incontinence products, feminine hygiene products as well as health care related products such as bandages and other wound dressings have a common goal of rapidly absorbing discharged body fluids such as blood, menses, urine and bowel movements. Typically such products will have a body contacting side and surface which is near or in contact with the wearer's skin, some type of absorbent core and a back sheet that will prevent the retained fluids from exiting the product and possibly soiling the surrounding areas including the wearer's clothes.

Thus, it is desirable for such products to rapidly take in fluids, pass them to subjacent layers in the product and provide air circulation adjacent the wearer's skin to promote skin wellness. Air circulation allows drying of the skin to prevent skin irritation such as diaper rash in the case of diapers, training pants and incontinence devices. Air circulation also provides increased comfort by allowing the body contacting material, often referred to as a top sheet or liner, to dry out. In addition, comfort and dryness can be further enhanced by minimizing the amount of the liner material that is in direct contact with the skin. This also facilitates a reduction in what is called "rewet" which is the backflow of fluid from the absorbent core onto the liner. As these are desirable attributes for such products, a number of materials and products have attempted to provide these results. For example, U.S. Pat. Nos. 5,667,619, 5,667,625 and 5,817,394 to Alikhan et al. disclose a fibrous laminate material as well as products incorporating the laminate and an apparatus for making the laminate material. Two fibrous layers are bonded together in a spaced apart bonding pattern comprising compacted bonding regions with lesser bonded fiber spans in between with substantially circular apertures formed in the bonded areas.

U.S. Pat. No. 7,386,924 to Muth et al. discloses a perforation device for perforating prebonded nonwovens having embossing points. Needles of a needle roller engage the prebonded nonwoven and perforate it and the perforated nonwoven undergoes further processing. U.S. Pat. No. 6,849,319 to Cree et al, discloses apertured nonwoven composites for use with absorbent articles. The composite top sheet includes a resilient three dimensional apertured formed film, a nonwoven web with small scale apertures and large scale apertures. The formed film is between the absorbent core and the body facing side. The formed film has a male side and a female side opposite the male side, and small scale apertures with a mesh count. The nonwoven web of fibers is between the formed film and the body facing side of the absorbent article. The large scale apertures extend through the nonwoven web and the formed film. The large scale apertures have a mesh count which is less than the mesh count of the small scale apertures.

U.S. Pat. No. 5,997,986 to Turi et al. discloses apertured plastic films which comprise a stretchable thermoplastic polymeric material having a plurality of microholes defined by a network of fiber-like elements. The films are produced by directing fluids, especially water, against the upper surface of a starting film in the form of columnar streams in a contact zone, while the film is supported on a backing element. EP 0 235 309 to Suzuki et al, discloses a facing for absorptive articles and the associated process for making it. The facing comprises a non-woven fabric having two layers of different fiber compositions with a first layer defining a surface to be in contact with the wearer's skin and having a pattern of apertures and a second layer defining a rear side with respect to the surface and having no apertures. In the process, the first layer is formed by subjecting a fibrous web to a high velocity water jet treatment on a support carrying thereon aperture formation elements, forming the second layer by subjecting a fibrous web to the aforementioned treatment or a heat fusion treatment, and simultaneously combining the first layer integrally with the second layer with either of the aforementioned treatments.

U.S. Pat. No. 5,895,380 to Turi et al. discloses absorbent products having a permeable cover made of a microperforated fibrillated thermoplastic film. The cover is characterized by having non perforate regions and perforate regions, the perforate regions having a plurality of microholes defined by a network of fiberlike elements, the perforate regions being, at least in part, at elevations that are higher than the nonperforate regions. The perforate regions are caused to be at higher elevations by methods such as tensioning the cover or by partly adhering the cover to the absorbent body of the product or by combinations thereof. Additional improvement of fluid acceptance and distribution properties are said to be obtained by corona discharge treatment of one side of the film before microperforating and by treating the microperforated film with surfactant.

European Patent No. 0 705 932 to James et al. discloses nonwoven fabrics having a fibrous background portion in one plane thereof and raised fibrous portions in another plane thereof. There may be two types of raised portions. In one type, the basis weight of the raised portion is substantially the same as the basis weight of the background portion. In another type of raised portion, the basis weight is greater than the basis weight of the background portion. The raised portions are joined to the background portion by a fibrous transition region. U.S. Pat. No. 4,333,979 to Sciaraffa et al. discloses a laminated fibrous web with differentially bonded layers as well as the method and apparatus for making such materials. The process provides a lightweight nonwoven web formed from continuous thermoplastic filaments substantially randomly oriented and pattern bonded, but further embossed under heat and pressure conditions resulting in an increased effective thickness providing softness and bulk while retaining other desirable physical properties such as strength. The bond pattern is composed of closely spaced point fused areas, while the subsequently applied embossing pattern comprises a gross pattern of much larger overall embossments.

U.S. Pat. No. 4,761,322 to Raley discloses a laminated fibrous web of differentially bonded layers as well as the method and apparatus for making such a web. The web is formed by the steps of forming a first fibrous layer of a first relatively higher density and bonding the fibers of the first fibrous layer to one another at a first relatively higher extent of bonding. A second fibrous layer is formed at a second relatively lower density and the fibers in the second fibrous layer are bonded to one another at a second relatively lower extent of bonding. Next, the first and second fibrous layers are bonded to each other at a third relatively lower extent as compared to the bonding of fibers to one another in the first fibrous layer.

U.S. Pat. No. 6,739,024 to Wagner discloses a method and device for producing a structured, voluminous nonwoven web or film. The web is produced by forming an unstructured web and subsequently processing this web using a pair of rollers. The pair of rollers consists of a positive roller having numerous positive bodies distributed over the roll sleeve surface and a negative roller having equally as numerous cavities. During the rolling process, the positive bodies engage with the cavities and stretch the unstructured web in the area of the roller engagements in such a way that a deep-drawn web structure with numerous cavities is produced. After the web has passed through a roller gap, the deformed web, still bonded to the positive roller, is brought into contact with a perforating tool and perforated. U.S. Pat. No. 3,542,634 to Such et al., discloses an apertured, bonded and differentially embossed nonwoven fabric. Deformable sheets of textile fibrous material are reformed by passing them through rolls engraved in a pattern of lands and grooves in such a way that a repeating pattern of three degrees of compression are effected; high compression where a land has traversed a land; intermediate compression where a land has traversed a grooves; and little or no compression where a groove has traversed a groove. The areas affected by the three degrees of compression are discrete and spaced apart areas of rhomboidal shape. The high compression areas may be bonded, for example, by the presence of thermoplastic fibers which are fused during embossing, or the high compression areas may be in the form of actual apertures in the fabric.

While the foregoing are examples of attempts to provide materials with the desired fluid handling properties, there is still a need for improved materials in this regard. The present invention is directed to a three-dimensional sheet material which can be used in this regard in conjunction with personal care absorbent articles including, but not limited to, diapers, training pants, incontinence garments, feminine hygiene products such as sanitary napkins and panty liners as well as other absorbent products including bandages and wound dressings.

SUMMARY OF THE INVENTION

To reduce the above mentioned technical problems, the present invention provides a three-dimensional sheet material which has a first layer of material having a top surface, a bottom surface and a thickness. The first layer of material defines a first plane, a second plane and a third plane which is located between the first plane and the second plane with at least a portion of the top surface being located in or adjacent the first plane and at least a portion of the bottom surface being located in or adjacent the second plane. The first layer of material has a plurality of first depressions beginning in or adjacent one of the first, second or third planes and which depend toward and terminate in or adjacent another of the first, second or third planes, and a plurality of second depressions which begin in or adjacent one of the first, second or third planes and which depend toward and terminate in or adjacent another of the first, second or third planes which is different from the plane in which the first plurality of depressions terminate.

If desired, the three-dimensional sheet material may have at least a portion of the plurality of first or second depressions define apertures therein. In addition, at least a portion of the plurality of the first or second depressions form liquid channels having a generally decreasing dimension as viewed in the direction from the first plane towards the second plane and which terminate in apertures to create liquid capillaries which permit liquid flow in the direction from the first plane towards the second plane. At least a portion of the plurality of first depressions can be uniformly-spaced over at least a portion of the first layer of material. Further, at least a portion of the plurality of second depressions can be uniformly-spaced over at least a portion of the first layer of material.

The first layer of material can have a basis weight of between about 8 grams per square meter and about 200 grams per square meter and a thickness of between about 0.1 millimeters and about 4 millimeters. The first layer of material can have an overall thickness between the first plane and the second plane of between about 0.3 millimeters and about 15 millimeters and an upper thickness between the first plane and the third plane of between about 0.05 millimeters and about 12 millimeters. The first layer of material can also have a lower thickness between the third plane and the second plane of between about 0.25 millimeters and about 8 millimeters.

To minimize the contact area of the three-dimensional sheet material, the surface area of a portion of the top surface of the first layer of material located in the first plane on a per unit area basis should be between about 20 percent and about 70 percent of the total surface area of the same portion of the top surface on a per unit area basis. Desirably, the three-dimensional sheet material is a fibrous nonwoven web.

To minimize wetness, it is desirable that the portion of the first layer of material located in the first plane be more hydrophobic than another portion of the first layer of material not located in the first plane.

The three-dimensional sheet materials of the present invention may be employed in a number of applications including as one or more layers of a personal care absorbent article. Such absorbent articles typically include a liquid pervious top sheet and a back sheet with an absorbent core located between the top sheet and the back sheet.

Depending on the material chosen to make the three-dimensional sheet material, it may be employed as one or all of the layers or components of such personal care absorbent articles.

DESCRIPTION OF THE DRAWINGS

A full and enabling disclosure of the present invention is set forth more particularly in the remainder of the specification, including reference to the accompanying figures, in which:

FIG. 3 is a top plan view of another three-dimensional sheet material according to the present invention.

FIG. 4 is a cross-sectional side view taken along line 4-4 of FIG. 3.

DETAILED DESCRIPTION

Figure 1:
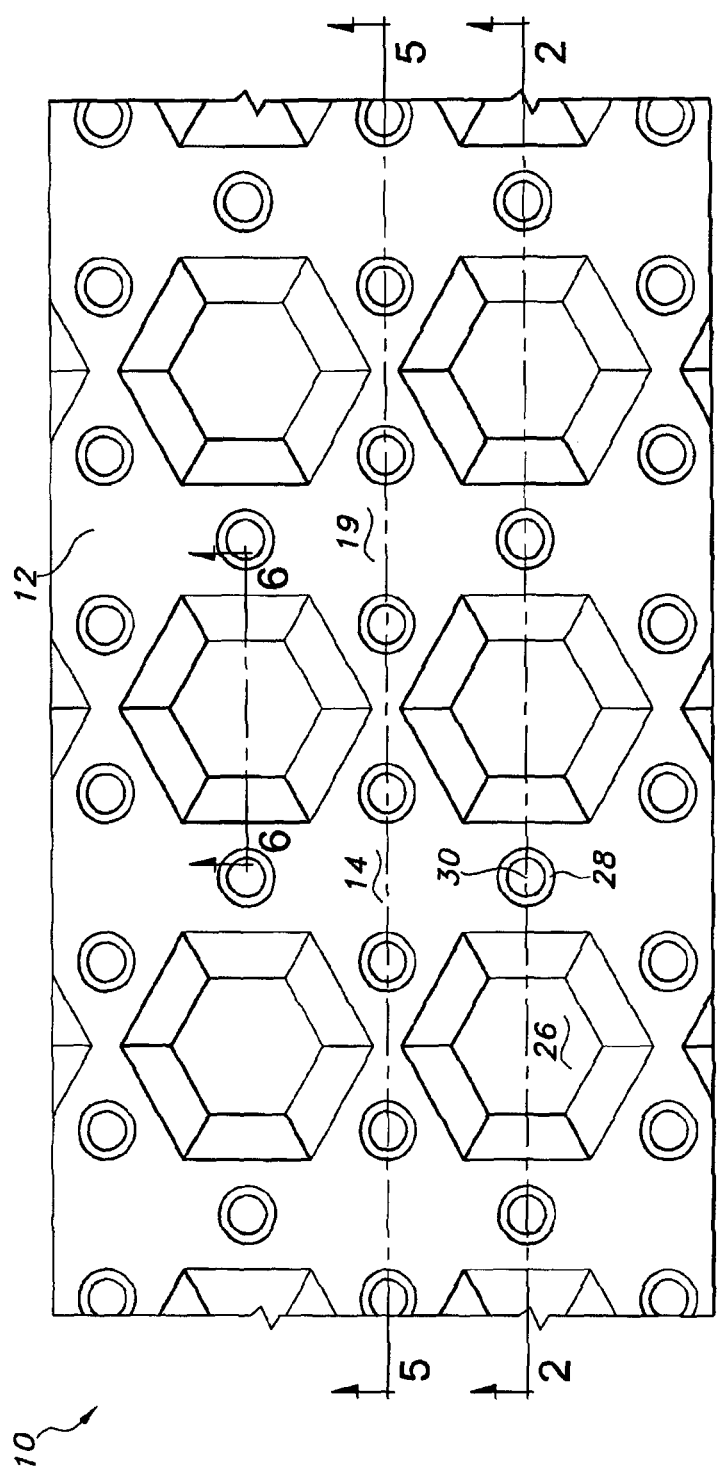
FIG. 1 is a top plan view of a three-dimensional sheet material according to the present invention.

Reference will now be made in detail to present embodiments of the invention, one or more examples of which are illustrated in the accompanying drawings. Each example is provided by way of explanation of the invention and not a limitation of the invention. In fact, it will be apparent that modifications and variations can be made in the present invention without departing from the scope or spirit thereof. For instance, features illustrated or described as part of one embodiment may be used on another embodiment to yield a still further embodiment. Additionally, parameters, measurements and elements of one example may be used alone or in combination with other parameters, measurements and elements of other examples of the present invention and may be used independently or in combination to support one or more of the claims appended hereto describing and claiming embodiments of the present invention. Thus, it is intended that the present invention covers these and other such modifications and variations as come within the scope of the appended claims and their equivalents.

Turning to FIGS. 1, 2, 5 and 6, there is shown a top plan view and various cross-sectional side views of a three dimensional sheet material 10 according to the present invention. The sheet material 10 comprises at least a first layer of material 12 which is subjected to embossing and, optionally, aperturing. This material 12 is any material which is able to pass liquids and gases, also referred to as being fluid permeable. In the context of personal care absorbent articles, the material 12 should be able to readily pass liquids such as urine and/or menses depending on the particular end application. Such is the case when the end application is a feminine care product such as a sanitary napkin, panty liner or other feminine care absorbent article. In addition, in certain instances it may be desirable for the material 12 to be able to pass portions of more solid-type materials such as runny bowel movements when the end application is for such products as diapers, training pants and incontinence garments. Further, the material 12 may be used for other applications where fluid transfer and absorption is necessary as in the case of bandages and other health care related products.

Due to the fact that the material 12 is subjected to embossing techniques to form a three-dimensional structure, the material 12 should be selected from a material that is able to hold a predetermined shape due to the application of pressure and optionally the use of heat. The application of pressure and heat can be achieved by a variety of methods including the use of engraved embossing rolls with optional heat and/or cooling as well as by the use of ultrasonics. In addition, it is desirable that the material be soft to the touch, especially when the material is being used as the body-contacting side of a personal care absorbent article which is designed to be worn against the skin. Both woven and nonwoven fibrous materials are thus within the scope of the present invention. Due to the need to be set in a three-dimensional shape, in some instances it is also desirable that the material 12 contain at least some material made from a polymeric plastic material and/or other materials that will take a pressure and/or heat set. Examples of such materials include, but are not limited to, polyolefins, polyesters, poly vinyl alcohol, polyurethane, nylon and the like. It is also possible to form woven materials and nonwovens materials from blends of various fibers made from varying materials, both natural and synthetic such as blends of various polymeric materials and blends of polymeric fibers and natural fibers such as cotton and wood pulp fluff, one example of the latter being staple coform materials which are a blend of staple fibers and wood pulp fibers. Still further, it is possible to use materials and webs that are made from all natural fibers such as cotton fibers and wood pulp fluff fibers. Other suitable nonwoven materials include spunbond materials, meltblown materials, staple fiber bonded carded webs including, but not limited to, through-air bonded carded webs and chemically bonded carded webs, airlaid webs, spunlace webs and hydroentangles webs. It is also possible to use composite materials such as multilayer materials including, but not limited to, laminates of layers of spunbond material and meltblown material.

Due to the fact that the materials of the present invention can be used for applications where fluid permeability is not critical or the material only has to be gas or vapor permeable, it is also possible to form the material 12 from a plastic film such as a thermoplastic film made from polymeric materials such as polyolefins and other materials that may be embossed using heat and/or pressure or ultrasonics so as to hold a three-dimensional shape. Further, such materials may be subject to aperturing, slitting and other processes to form fluid transport passages through the film layer from one side to the other. When this happens, the film materials made according to the present invention are also suitable for use in the foregoing personal care absorbent articles and other absorbent articles including bandages and other health care related products as the body contacting surface of the product.

Still further, it is possible to form the material 12 from other multi-layered structures such as two or more layers of nonwovens or a combination of nonwoven and film layers. Such multi-layer structures may be formed in advance of applying the three-dimensional embossing of the present invention or they may be joined as a result of the three-dimensional embossing process.

Turning again to FIGS. 1, 2, 5 and 6, there is shown a first layer of material 12, which has a top surface 14, a bottom surface 16 and a thickness 18. The first layer of material 12 defines a first plane 20, a second plane 22 and an intermediate or third plane 24 located between the first plane 20 and the second plane 22. The first plane 20 is shown drawn adjacent and touching the top surface 14 which is the exterior surface of the material 12 on one side while the second plane 22 is shown drawn adjacent and touching the bottom surface 16 which is the exterior surface of the material 12 on the other side. The intermediate or third plane 24 is shown being drawn adjacent an intermediate surface of the material 12 located between the two exterior surfaces.

Figure 2:
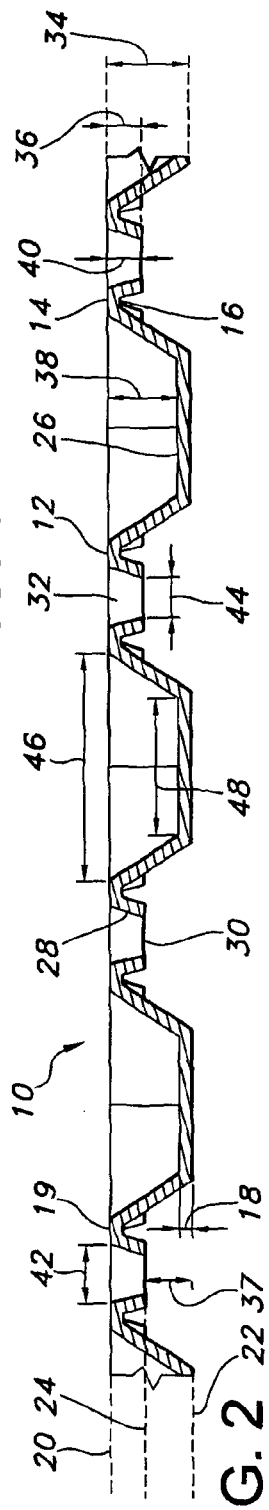
FIG. 2 is a cross-sectional side view taken along line 2-2 of FIG. 1.
Figure 5:
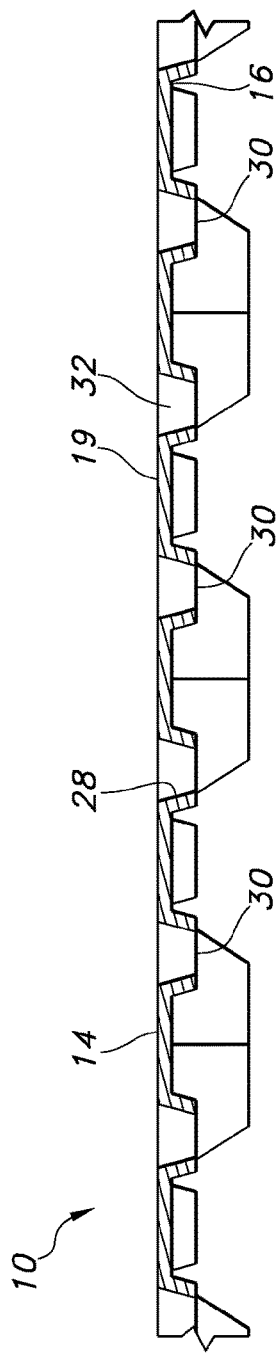
FIG. 5 is a cross-sectional side view taken along line 5-5 of FIG. 1.
Figure 6:
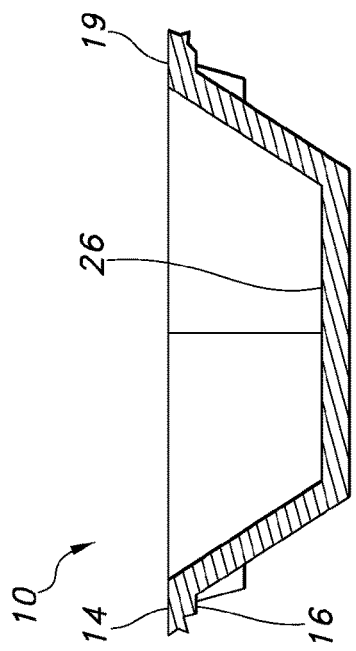
FIG. 6 is a cross-sectional side view taken along line 6-6 of FIG. 1.
Figure 7:
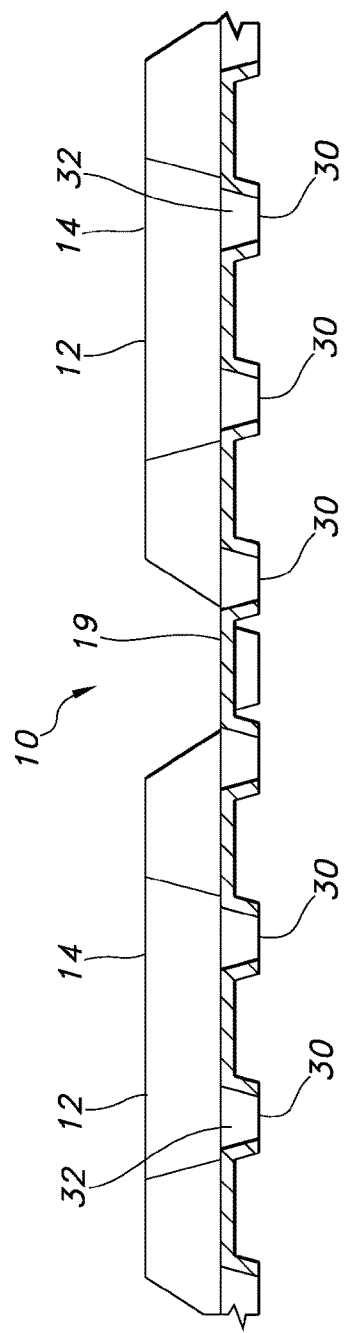
FIG. 7 is a cross-sectional side view taken along line 7-7 of FIG. 3.
Figure 8:
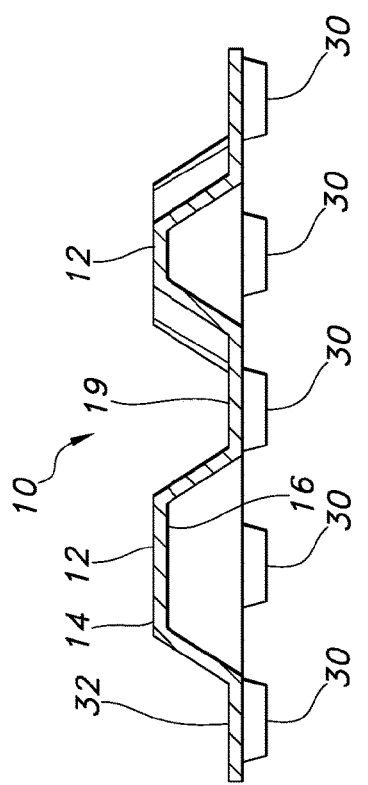
FIG. 8 is a cross-sectional side view taken along line 8-8 of FIG. 3.

To provide the three-dimensional shape of the present invention, the material 12 is provided with a plurality of first depressions 26 extending downwardly from the first plane 20 towards the second plane 22. At least a portion of the first depressions 26 terminate in or adjacent the second plane 22. The material 12 also includes a plurality of second depressions 28 which extend downwardly from the first plane 20 towards the second plane 22 with at least a portion of the plurality of second depressions 28 terminating intermediate the first 20 and second 22 planes. As shown in FIG. 2, a plurality of the second depressions 28 terminate at a common depth and thus define the intermediate or third plane 24 as they terminate in or adjacent the third plane 24. The plane 24 is shown drawn adjacent and touching the bottom of the depressions 28 in FIG. 2. While not shown, it is also contemplated to be within the scope of the present invention to provide yet further planes and further depressions emanating from such additional planes and terminating at or in other planes.

In addition to having differing depth depressions, it is possible to create apertures in the material 12. As shown in FIG. 2, at least a portion of the plurality of second depressions 28 are provided with or define apertures 30 which are located in or adjacent the intermediate plane 24. Note, however, that it is also possible to provide apertures in first depressions 26. Additionally, it is possible to provide apertures in other areas of the material 12 including the land area 19 (not shown). Further, it is possible to form these apertures not only in the bottom of the depressions but also in the side walls of the depressions (not shown). Still further, it is possible to form materials with common or variable aperture sized in any of the areas including the first depressions 36, the second depressions 38 and the land areas 19.

At least a portion of the depressions (either 26 or 28) can form liquid channels 32 from one plane to the other. The walls of the depressions can be straight or angled. The flow of liquids from one plane to the other can be facilitated by aperturing either or both of the depressions and forming the walls of the depressions with a generally decreasing dimension from one plane to the other. By decreasing the dimension, a capillary effect is formed which promotes fluid/liquid flow from one plane to the other and also resists flow in the opposite direction. As shown in FIG. 2, there are liquid channels 32 which extend from the first plane 20 to the intermediate plane 24 with walls that have a generally decreasing dimension from the first plane 20 to the intermediate plane 24.

By forming the plurality of first 26 and second 28 depressions in the material 12, the actual portion of the material 12 remaining in the first plane 20 is reduced which is desirable when the three-dimensional sheet material 10 according to the present invention is used as a body-contacting material in an absorbent article such as a diaper, diaper pant, training pant, incontinence device or a feminine hygiene article such as a sanitary napkin, panty liner and the like. From a comfort standpoint, minimizing skin contact with the wearer has several advantages. First, minimizing body contact surface reduces the amount of abrasive surface in contact with the wearer. Second, minimizing the body contacting surface reduces the amount of material that may be soiled or wet which causes discomfort to the wearer. When liner materials in absorbent articles are insulted with body fluids such as urine, menses and bowel movements, it is desirable to move as much of such body fluids away from the skin of the wearer as quickly as possible. By providing and maximizing the amount of depressions and/or apertures in the material 12, the amount of skin contact area remaining in or adjacent the first plane 20 is minimized. As a result, an overall product is provided which is more pleasing to the wearer and facilitates skin wellness as there is less wet, soiled product in contact with the wearer.

The overall thickness 18 of the sheet material 12 will depend on the particular end application. In the context of personal care absorbent articles, the three-dimensional sheet material 10 can be used as a part of the body side liner or layer, as the back sheet, especially when the sheet material 12 is a film and in particular a non-apertured film. The first layer of material 12 can also be used as one of the intermediate layers of a personal care absorbent article including, the absorbent core or one or more of the other layers of such products including what is commonly termed the surge or transfer layer which is a layer between the absorbent core and the body side liner or top sheet. Furthermore, it can be used as an additional layer between the absorbent core and the back sheet.

Thus, for the embodiment shown in FIGS. 1, 2, 5 and 6, the three-dimensional sheet material 10 comprises a first layer of material 12 having a top surface 14, a bottom surface 16 and a thickness 18. The first layer of material 12 defines a first plane 20, a second plane 22 and third plane 24 located between the first plane 20 and the second plane 22. At least a portion of the top surface 14 is located in or adjacent the first plane 20 and at least a portion of the bottom surface 16 is located in or adjacent the second plane 22. The first layer of material 12 has a plurality of first depressions 26 depending from the first plane 20 toward the second plane 22. At least a portion of the plurality of first depressions 26 terminate in or adjacent the second plane 22. The first layer of material 12 also has a plurality of second depressions 28 depending from the first plane 20 toward the second plane 22. At least a portion of the plurality of second depressions 28 terminate in or adjacent the third plane 24. Any or all of the first depressions 26 or the second depressions 28 can be apertured as well as the land areas 19.

Referring now to FIGS. 3, 4, 7 and 8 of the drawings, there is show another three-dimensional sheet material 10 according to the present invention. As with the first embodiment, the same references numerals are used for and describe like elements. The main difference is that in this embodiment, the plurality of first depressions 26 can be viewed as depending upwardly from the intermediate or third plane 24 in the direction of the first plane 20 while the plurality of second depressions 28 depend downwardly from the intermediate plane 24 in the direction of the second plane 22. Thus the terms "depend", "depending" and variations of the same can mean or define a direction either up or down from a given plane.

Thus, for the embodiment shown in FIGS. 3, 4, 7 and 8, the three-dimensional sheet material 10 comprises a first layer of material 12 having a top surface 14, a bottom surface 16 and a thickness 18 with first layer of material 12 defining a first plane 20, a second plane 22 and third plane 24 located between the first plane 20 and the second plane 22. At least a portion of the top surface 14 is located in or adjacent the first plane 20 and at least a portion of the bottom surface 16 is located in or adjacent the second plane 22. The first layer of material 12 has a plurality of first depressions 26 depending from the third plane 24 toward the first plane 20 and at least a portion of the plurality of first depressions 26 terminate in or adjacent the first plane 20. The first layer of material 12 also has a plurality of second depressions 28 depending from the third plane 24 toward the second plane 22 and at least a portion of the plurality of second depressions 28 terminate in or adjacent the second plane 22. Any or all of the first depressions 26 or the second depressions 28 can be apertured as well as the land areas 19.

Consequently, when viewing the embodiments from all of the Figures, it can be seen that the three-dimensional sheet material 10 of the present invention can comprise a first layer of material 12 having a top surface 14, a bottom surface 16 and a thickness 18. The first layer of material 12 defines a first plane 20, a second plane 22 and a third plane 24 located between the first plane 20 and the second plane 22. At least a portion of the top surface 14 is located in or adjacent the first plane 20 and at least a portion of the bottom surface 16 is located in or adjacent the second plane 22. The first layer of material 12 has a plurality of first depressions 26 beginning in or adjacent one of the first 20, second 22 or third 24 planes which depend toward and terminate in or adjacent another of the first 20, second 22 or third 24 planes. The first layer of material 12 also has a plurality of second depressions 28 beginning in or adjacent one of the first 20, second 22 or third 24 planes which depend toward and terminate in or adjacent another of the first 20, second 22 or third 24 planes which is different from the plane in which the first plurality of depressions 26 terminate. Any or all of the first depressions 26 or the second depressions 28 can be apertured as well as the land areas 19.

When the three dimensional sheet material 10 of the present invention is used in personal care absorbent articles it will have a thickness 18 between about 0.1 millimeters and about 4 millimeters, more desirably between about 0.3 millimeters and about 2 millimeters and most desirably between about 0.5 millimeters and about 1.5 millimeters. For purposes of the present invention, the term "between" as used throughout is meant to be inclusive of the end numbers used in the range.

As to basis weight, again the actual basis weight can vary depending on the end application. In the context of personal care absorbent articles, the first layer of material 12 will have a basis weight of between about 8 grams per square meter (gsm) and about 200 gsm, more desirably between about 16 gsm and about 100 gsm and most desirably between about 22 gsm and about 50 gsm. The basis weight of a nonwoven web can be determined in accordance with Federal Test Method 5041, Standard No. 191A.

Once the three-dimensionality has been imparted to the sheet material 12, the structure will define an overall thickness 34 between the first plane 20 and the second plane 22 of between about 0.3 millimeters and about 15 millimeters, more desirably between about 1 millimeter and about 7 millimeters and most desirably between about 1.5 millimeters and about 5 millimeters.

The structure will also define an upper thickness 36 between the first plane 20 and the intermediate/third plane 24 of between about 0.05 millimeters and about 12 millimeters, more desirably between about 0.15 millimeters and about 5 millimeters and most desirably between about 0.25 millimeters and about 4 millimeters.

As between the intermediate/third plane 24 and the second plane 22, the structure will define a lower thickness 37 of between about 0.25 millimeters and about 8 millimeters, more desirably between about 0.85 millimeters and about 6 millimeters and most desirably between about 1.25 millimeters and about 3 millimeters.

The plurality of first depressions 26 shown in FIGS. 1, 2, 5 and 6 define a first depression depth 38 between the first plane 20 and the inner ("inner" meaning the surface closest to the previously referenced plane) surface of the first depressions 26. For the embodiment shown in FIGS. 3, 4, 7 and 8, the first depression depth 38 is defined between the intermediate or third plane 24 and the inner surface of the first depressions 26 adjacent the first plane 20. The first depression depth 38 will have a range of between about 0.2 millimeters and about 8 millimeters, more desirably between about 0.6 millimeters and about 4 millimeters and most desirably between about 1 millimeters and about 3 millimeters.

The plurality of second depressions 28 shown in FIGS. 1, 2, 5 and 6 define a second depression depth 40 between the first plane 20 and the intermediate plane 24. For the embodiment shown in FIGS. 3, 4, 7 and 8, the second depression depth 40 is measured between the top and open bottom ends of the depressions 28 and the value includes the thickness 18 of the first layer of material 12 adjacent the intermediate or third plane 24. The second depression depth 40 will have range of between about 0.15 millimeters and about 6 millimeters, more desirably between about 0.45 millimeters and about 3 millimeters and most desirably between about 0.75 millimeters and about 2.25 millimeters.

Note that the first depression depth 38 does not include the thickness 18 of the sheet material 12 at the bottom of the first depressions 26. As to the second depression depth 40, due to the fact that the second depressions are apertured, the second depression depth 40 is measured to the point at which the open depressions terminate whereas if the second depressions were not apertured, the depression depth would be measured to the same point as described above with respect to the first depressions 26, that is to the inner surface of the depression 28.

In addition to the thicknesses and depths of the three-dimensional sheet material 10 described above, the opening measurements of the first and second depressions 26 and 28 can also be measured. The first depressions 26, if they have non-parallel side walls, will have a first opening size 46 adjacent the first plane 20 and a second opening size 48 adjacent the bottom of the first depressions 26 adjacent the intermediate plane 24. Both opening sizes (as with the second depressions 28) are measured along the major axis of the openings (the longest straight line that can be drawn between two edges of the opening generally parallel to the nearest plane to the respective opening). If the sides of the openings are generally parallel, the upper and lower opening dimensions will be substantially similar. The same is also true for the second depressions 28 in both FIGS. 2 and 4. They will have a third opening size 42 adjacent the first plane 20 and a fourth opening size 44 adjacent the third plane 24.

The first opening size 46 can have a major axis dimension of between about 2 millimeters and about 30 millimeters, more desirably between about 2.5 millimeters and 25 millimeters and most desirably between about 3 millimeters and about 20 millimeters. The second opening size 48 can have a major axis dimension of between about 1 millimeter and about 29 millimeters, more desirably between about 1.5 millimeters and about 24 millimeters and most desirably between about 2 millimeters and about 19 millimeters.

The third opening size 42 of the second depressions 28 can have a major axis dimension of between about 0.2 millimeters and about 10 millimeters, more desirably between about 0.3 millimeters and 5 millimeters and most desirably between about 0.4 millimeters and about 3 millimeters. The fourth opening size 44 of the second depressions 28 can have a major axis dimension of between about 0.1 millimeters and about 9.9 millimeters, more desirably between about 0.2 millimeters and about 4.9 millimeters and most desirably between about 0.3 millimeters and about 2.9 millimeters.

When the bottoms of the first and second depressions 26 and 28 are apertured, the aperture sizes may be equal to or smaller than the respective second opening size 42 and fourth opening size 44. The apertures, whether in the depressions 26, 28 or the land areas 19 (not shown), may have any size suitable for the intended use. For lower viscosity fluids such as urine, the apertures may be smaller in size while for higher viscosity fluids such as menses and runny bowel movements, it is generally desired that the aperture sizes be larger. The aperture sizes can be between about 0.1 millimeters and about 30 millimeters, more desirably between about 0.2 millimeters and 25 millimeters and most desirably between about 0.3 millimeters and about 20 millimeters.

The shape of the depressions 26 and 28 can be any shape suitable for the particular end application. In FIG. 1 of the drawings the plurality of first depressions 26 are shown as being hexagonal in shape and the plurality of second depressions 28 are shown as being round. In FIG. 3 of the drawings, the first plurality of depressions 26 are shown as more elliptical in shape with bulbous ends, otherwise known as being "dog bone" in shape while the second plurality of depressions 28 are again shown as being round or circular. Other shapes may also be used including, but not limited to, square, rectangular, triangular, poly-sided, oval, elliptical, star-shaped, as more decorative designs such as flowers, animals, etc. as well as combinations of the foregoing and other shapes.

Note too that while the bottom-most portions of the depressions shown in the drawings are flat or substantially flat, it is also possible to have other shaped surfaces as well. For example, the bottom-most portions of the depressions may be rounded and such rounding may be concave or convex (not shown).

The spacing of the depressions 26 and 28 as to themselves or each other may be varied depending on the particular end use and may be random or uniform. A uniform pattern can be defined as being one that is discernable to the human eye either with or without magnification. The uniformity will be exemplified by there being a common dimension or spacing between the depressions. For example, if there is a common center-to-center spacing or an edge-to-edge spacing between depressions that exists in at least 20% of a selected area of the material 12, then the material can be defined as being "uniform". In FIGS. 1 and 3, the spacing of both the first plurality of depressions 26 and the plurality of second depressions 28 are uniform.

As to the embodiment of the three-dimensional sheet material 10 in the examples with the embossing pattern corresponding to that shown in FIG. 3, each of the "dog bone" depressions 26 have an overall length along their major axes of approximately 10.36 millimeters and a width at the widest portion of the dog bone ends of approximately 3.33 millimeters. The end-to-end spacing between the dog bone depressions lying along a longitudinal line aligning with the longitudinal centerlines of the dog bone depressions is approximately 4.3 millimeters. As to the offset parallel rows of the dog bone depressions, the spacing is approximately 4.75 millimeters as measured from longitudinal centerline to longitudinal centerline of the dog bone depressions in one row and another.

Once the three-dimensional sheet material 10 has been given its three-dimensional shape, it may be desirable to make the remaining portion of the top surface 14 of the first layer of material 12 located in or adjacent the first plane 20 more hydrophobic than the remainder of the three-dimensional sheet material 10. The advantage of this is that when the sheet material 10 is used, for example, as a body side liner material in an absorbent article such as a diaper or feminine hygiene product, the portion of the sheet material most adjacent the wearer's skin will tend to resist being wetted. As a result, body exudates such as urine, menses, blood and bowel movements will tend to want to move off this area and flow down into the depressed areas and apertures thus keeping the wearer's skin drier, more comfortable and less likely to become irritated. If the first layer of material 12 is naturally hydrophobic, then no treatment will be necessary though it may be desirable to make the other portions of the first layer of material 12 more hydrophilic. Conversely, if the first layer of material 12 is hydrophilic, it may be desirable to treat the areas of the top surface 14 in or adjacent the first plane 20 with a hydrophobic treatment. Both hydrophilic and hydrophobic treatments for materials used in personal care absorbent articles are well known. An example of hydrophilic treatment includes, but is not limited to, a hydrophilic spinning finish designated (THL-PP-2028 which is manufactured and sold by (Changzhou) Lingda Chemical Co., Ltd. of Jiangsu, China. An example of hydrophobic treatment includes, but is not limited to, hydrophobic fiber lubricants designated THL-2508A manufactured and sold by (Changzhou) Lingda Chemical Co., Ltd, of Jiangsu, China. The terms "hydrophilic" is used to refer to a material having a contact angle of water in air of less than 90 degrees. The term "hydrophobic" refers to a material having a contact angle of water in air of at least 90 degrees. Contact angle measurements can be determined as set forth in Robert J. Good and Robert J. Stromberg, Ed., in "Surface and Colloid Science—Experimental Methods," Vol. 11, (Plenum Press, 1979), which is hereby incorporated by reference in a manner that is consistent herewith.

The first layer of material 12 has a total surface area but due to the embossing only a portion of the total surface area of the top surface 14 resides in or adjacent the first plane 20. To minimize the portion of the top surface 14 in contact with the wearer's skin, especially when the three-dimensional sheet material 10 is employed as the body side or top sheet of an absorbent article, it is desirable that the surface area of a portion of top surface 14 of the first layer of material 12 located in the first plane 20 on a per unit area basis be between about 20 percent and about 70 percent of the total surface area of the same portion of the top surface 14 on a per unit area basis, more desirably between about 30 percent and about 50 percent and most desirably between about 30 percent and about 40 percent. Thus, as with any of the parameters set forth herein, if any portion of the three-dimensional sheet material 10 has a portion that satisfies this parameter, it is deemed to be within the scope of the present invention.

To form the three-dimensional sheet material of the present invention, conventional intermeshing male and female embossing rolls may be used. For example, to make the three-dimensional sheet material 10 of FIGS. 1 and 3, a male embossing roll can be formed with protrusions mimicking the cross-sectional pattern of both the first depressions 26 and the second depressions 28. These in turn can mate with a female embossing roll which has formed therein, the mating recessed pattern of the male roll. In addition, if apertures are to be made, the protrusions for making the second depressions on the male roll can be fitted with piercing points which fit into mating holes in the female embossing roll so that when the first layer of material 12 is forced between the two mating rolls, the three-dimensional shape will be formed and the sharp piercing points will puncture the material 12 as the piercing points project into the receiving holes in the female roll.

As stated at the outset, the three-dimensional shape set in the material 12 can be due solely to mechanical pressure. Alternatively, either or both of the male and female embossing rolls may be heated and/or cooled to facilitate the formation and set of the three-dimensional shape. Additionally, ultrasonic equipment using horns and anvils can be used to impart the desired embossing pattern.

If it is desired to coat the top surface 14 of the material 12 to make it more hydrophobic, a coating roller or other suitable equipment can be placed adjacent the female embossing roller just downstream of the male roller to apply a coating of desired hydrophobic or hydrophilic material to the top surface 14 of the material 12. In addition to making embossing rolls where one roll is strictly a male roll and the other is exclusively a female roll, it is also possible to form mating intermeshing rolls wherein male and female portions are formed on both of the rolls. For example, with reference to the embodiment shown in FIG. 3, one roll may be formed with male projections corresponding to the formation of the first depressions 26 and the other roll may have male projections corresponding to the formation of the second depressions 28 and the aperture 30 with each of the rolls having formed therein the corresponding and mating female portions of the projections.

Figure 9:
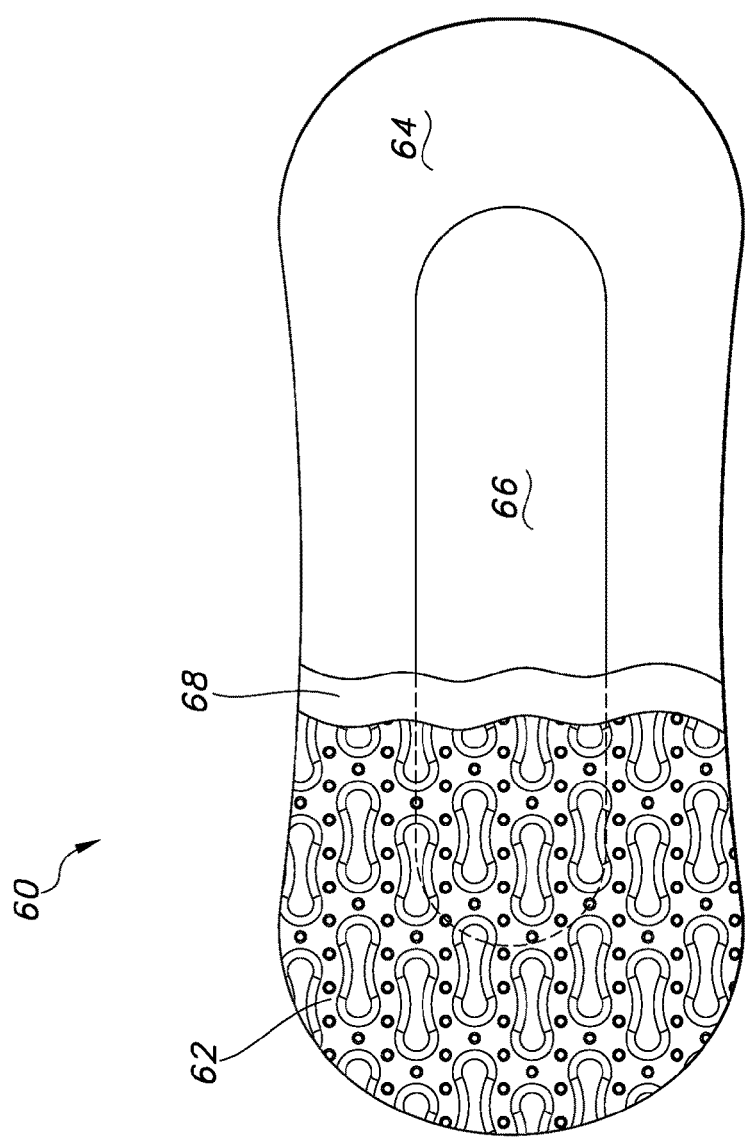
FIG. 9 is a cut-away top plan view of an absorbent article, in this case, a feminine hygiene product utilizing the three-dimensional sheet material of the present invention as the top sheet or body side liner.

The three-dimensional sheet material 10 can be used in a wide variety of applications including, but not limited to, absorbent articles and in particular, personal care absorbent articles designed to be worn against or around the body to absorb body exudates. Turning to FIG. 9 of the drawings there is shown an exemplary absorbent article 60, in this case a sanitary napkin, which employs the three-dimensional sheet material 10 as the liquid pervious top sheet 62. The article 60 also includes a liquid impervious back sheet 64 which is typically joined to the top sheet 62 either directly or indirectly and an absorbent core 66 is disposed between the top sheet 62 and the back sheet 64. Optionally, the article 60 may include other layers such as what is termed a surge layer, transfer layer or spacer layer 68 located between the absorbent core and the top sheet 62. While the three-dimensional sheet material 10 is shown as being used for the top sheet 62, it may be used for any of the other layers including, but not limited to, the surge layer 68, the absorbent core 66 and the back sheet 64.

Test Methods

The measurements for the parameters set forth herein, including the overall thickness 34, the upper thickness 36, the lower thickness 37, the first depression depth 38, the second depression depth 40, the first opening size 46, the second opening size 48, the third opening size 42, the fourth opening size 44, thickness 18 and aperture sizes measurements can be determined for samples of the representative materials using optical microscopy techniques as set forth below.

Images of the materials were taken in a cross-section view similar to that of line 2-2 of FIGS. 1 and 4-4 in FIG. 3 of the drawings for sample materials. (Note, however, that other sections can be taken to accommodate measurements of other desired parameters.) To accomplish this, an initial sample of the material to be tested was cut to a dimension of approximately 35 millimeters×35 millimeters. Using forceps, the sample was then immersed for thirty (30) seconds in liquid nitrogen to freeze and stiffen the sample prior to cutting. Next, using an Extra-Keen Teflon®-coated single edge surgical razor available from Electron Microscopy Sciences Inc. (Part #71971), a specimen was cut from the sample while viewing the sample through a Leica Wild Model 10 stereo-microscope at 10× magnification to ensure accurate positioning of the blade. The specimen cut from the sample was 25 millimeters long by 5 millimeters wide. The specimen was cut to be viewed and photographed along the above-mentioned lines of FIGS. 1 and 3 so that the cross-section and thickness of the material could be viewed and measured. The microscope field of view was 1.0 centimeter wide by 1.25 centimeters long. (Other comparable cutting razors and stereo-microscopes can be used to accomplish the foregoing tasks.)

The specimen was then attached to small piece of standard dull black construction paper. A piece of the construction paper was cut to a size with a length longer than the specimen length (in this case approximately 30 millimeters) and a width which is larger than the specimen width (in this case approximately 25 millimeters). Clear double-sided adhesive tape was then applied to one side of the construction paper and the specimen was laid down onto the construction paper with as little pressure as possible and overlapping a long edge of the adhesive tape such that the long dimension of the specimen (25 millimeters) was parallel to the length of the construction paper (the 30 millimeter length) and such that a small portion (at least one to two millimeters) of the 5 millimeter width of the specimen was extending beyond the edge of the adhesive tape and construction paper. Thus, one side of the specimen was adhesively attached to the construction paper. This exposed edge was ultimately the edge from which the photomicrograph was taken so that the thickness and cross-sectional shape of the specimen can be viewed.)

The other side of the construction paper mount not containing the specimen was then adhesively attached in a vertical position to a mounting block with any shiny surfaces of the mount being covered with additional dull black construction paper to reduce glare. As a result, the exposed and non-overlapping edge of the specimen was available for photographing to view the thickness and cross-sectional shape of the material.

The vertically mounted and extending specimen was then placed onto a horizontal work surface and the specimen was illuminated from above, at a slight angle from vertical, using a suitable light source (in this case a Volpi Model NCL 150 fiber-optic lamp with a 150 watt bulb available from Volpi USA, Auburn, N.Y.). The angle of the light source was adjusted to minimize glare. Images were then taken from a vertical overhead position using a Leica M420 zoom photo-stereomicroscope available from Leica Microsystems GmbH of Wetzlar, Germany at an optical magnification of 3.6× and at a distance of approximately 16 centimeters from the top, exposed edge of the specimen so as to capture the thickness and cross-section of the three dimensional material. The photo-stereomicroscope was mounted perpendicularly to the work surface.

Images from the photo-stereomicroscope were then captured using a Sony DXC-390 HD video camera equipped with a ⅓ inch (diagonal measurement) CCD chip available from Sony Electronics, Inc., New York, N.Y. and these images where then sent to, viewed and measurements taken using a Boeckeler Model VIA-100 video measurement system available from Boeckeler Instruments, Inc. of Tuscan, Ariz. The Boeckeler equipment was connected to the Sony video camera and the images from the Boeckeler equipment were viewed on a standard computer video monitor using standard video connection cables. The Boeckeler equipment was operated in conformance with its operations manual. Image lines were imposed to replicate the planes 20, 22 and 24 described and shown in the present specification and drawings using the Boeckler equipment. Other measurements relative to other parameters of the present invention can be accomplished in a similar manner.

Prior to taking any measurements, a standard image calibration was performed using an optical stage micrometer suitable for use with optical microscopes. In this case a Model S22 optical stage micrometer (2 mm/10-micron increments) available from Pyser-SGI Ltd. of Edenbridge, Kent, UK was used for calibration purposes. Image lines were then placed on the images of the specimen and the lines could be positioned with 0.016 mm (16 micrometer) accuracy. The positions of the respective planes in an image were determined by visual assessment and measurement lines were placed accordingly. The placement of the lines was done in accordance with the Boeckeler operations manual.

Figure 10A:
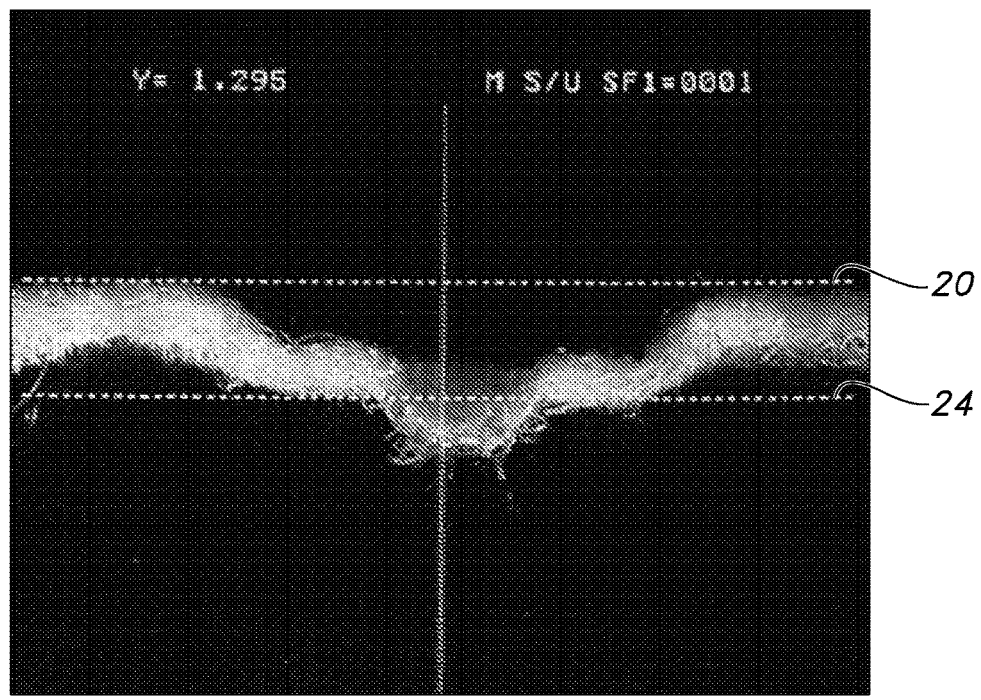
FIGS. 10A and 10B are photomicrographs of cross-sections of three dimensional sheet material according to the present invention.
Figure 10B:
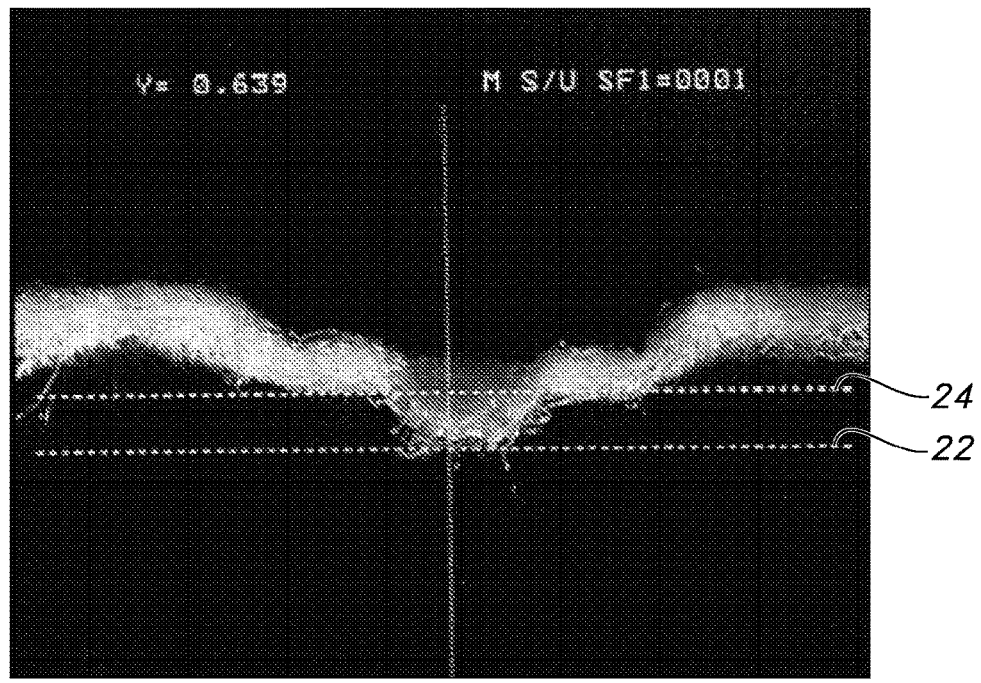

Distance measurements for the specimen were taken between planes 20 and 24 and planes 24 and 22 as shown in FIGS. 2 and 4 of the drawings which are represented in FIGS. 10A and 10B. Measurements were collected from four separately mounted specimens taken from four separate samples of the material being tested. The four measurements were recorded and then averaged and the four measurements and the average were reported in millimeters.

EXAMPLES

To illustrate the present invention, a series of sample materials were made as set forth in further detail below. In addition, sample products, in this case sanitary napkins were made with the three-dimensional sheet material 10 used as the bodyside liner, the surge layer and the absorbent core.

Example 1

Two sample materials were made according to the present invention, one with the embossing and aperturing pattern of FIG. 1 and a second with the embossing and aperturing pattern of FIG. 3 of the drawings. Both samples used the same first layer of material 12 which was a 24 gsm through air bonded carded web manufactured by Beijing Dayuan Nonwoven Fabric Co., Ltd. of Beijing, China. The carded web, designated FW540, was made from 38 millimeter, 2 denier polyethylene sheath/polyester core bicomponent fibers designated by the manufacturer as IWET2/38aaA fibers.

Measurements were made of the upper thickness 36 for the samples and reported in millimeters. For the sample with the embossing design according to FIG. 1, the upper thickness values were 0.410, 0.410, 0.492 and 0.475 mm for an average of 0.447 mm. For the sample with the embossing design according to FIG. 3, the upper thickness values were 1.148, 1.098, 1.000 and 0.984 mm for an average of 1.058 mm.

Measurements also were made of the lower thickness 37 for the samples and reported in millimeters. For the sample with the embossing design according to FIG. 1, the lower thickness values were 0.836, 0.705, 0.574 and 0.721 mm for an average of 0.709 mm. For the sample with the embossing design according to FIG. 3, the lower thickness values were 0.311, 0.393, 0.410 and 0.279 mm for an average of 0.348 mm.

The three-dimensional sheet materials so made are suitable for multiple uses including both a top sheet material 62 and a surge layer 68 in an absorbent article 60 as described above.

Example 2

Two sample materials were made according to the present invention, one with the embossing and aperturing pattern of FIG. 1 and a second with the embossing and aperturing pattern of FIG. 3 of the drawings. Both samples used the same first layer of material 12 which was a 22 gsm through air bonded carded web manufactured by Beijing Dayuan Nonwoven Fabric Co., Ltd. of Beijing, China under the trade designation BW020. The carded web was made from polyethylene sheath, polypropylene core concentric bicomponent staple fibers having a denier of 2 and a staple length of 38 millimeters.

Measurements were made of the upper thickness 36 for the samples and reported in millimeters. For the sample with the embossing design according to FIG. 1, the upper thickness values were 0.525, 0.459, 0.492 and 0.508 mm for an average of 0.496 mm. For the sample with the embossing design according to FIG. 3, the upper thickness values were 0.623, 0.803, 0.721 and 0.689 mm for an average of 0.709 mm.

Measurements also were made of the lower thickness 37 for the samples and reported in millimeters. For the sample with the embossing design according to FIG. 1, the lower thickness values were 0.262, 0.295, 0.180 and 0.393 mm for an average of 0.283 mm. For the sample with the embossing design according to FIG. 3, the lower thickness values were 0.607, 0.492, 0.328 and 0.377 mm for an average of 0.451 mm.

The three-dimensional sheet materials so made are suitable for multiple uses including both a topsheet material 62 and a surge layer 68 in an absorbent article 60 as described above.

Example 3

Two sample materials were made according to the present invention, one with the embossing and aperturing pattern of FIG. 1 and a second with the embossing and aperturing pattern of FIG. 3 of the drawings. Both samples used the same first layer of material 12 which was a 60 gsm airlaid nonwoven web manufactured by Fiberweb (China) Airlaid Company Limited of Tianjin, China. It was a blend of 70% by weight cellulosic fibers, 20% by weight polyolefin bicomponent staple fibers and 10% by weight latex.

Measurements were made of the upper thickness 36 for the samples and reported in millimeters. For the sample with the embossing design according to FIG. 1, the upper thickness values were 1.082, 1.016, 0.902 and 0.836 mm for an average of 0.959 mm. For the sample with the embossing design according to FIG. 3, the upper thickness values were 1.295, 1.443, 1.508 and 1.574 mm for an average of 1.455 mm.

Measurements also were made of the lower thickness 37 for the samples and reported in millimeters. For the sample with the embossing design according to FIG. 1, the lower thickness values were 0.279, 0.492, 0.262 and 0.295 mm for an average of 0.332 mm. For the sample with the embossing design according to FIG. 3, the lower thickness values were 0.639, 0.541, 0.475 and 0.443 mm for an average of 0.525 mm.

The three-dimensional sheet materials so made are suitable for multiple uses including an absorbent article 60 as described above, especially in the context of an absorbent core 66.

Example 4

Two sample materials were made according to the present invention, one with the embossing and aperturing pattern of FIG. 1 and a second with the embossing and aperturing pattern of FIG. 3 of the drawings. Both samples used the same first layer of material 12 which was a 30 gsm 100% cotton fiber hydro-entangled web manufactured by Unitika Ltd. of Osaka, Japan and available under the trade designation C30-70-#25.

The three-dimensional sheet materials so made are suitable for multiple uses including an absorbent article 60 as described above, especially in the context of an absorbent core 66.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

We claim:

1. A three-dimensional sheet material comprising a first layer of material having a top surface, a bottom surface and a thickness, said first layer of material defining a first plane, a second plane and third plane located between said first plane and said second plane with at least a portion of said top surface being located in or adjacent said first plane and at least a portion of said bottom surface being located in or adjacent said second plane, said first layer of material having a plurality of first depressions depending from said third plane toward said first plane, at least a portion of said plurality of first depressions terminating in or adjacent said first plane, wherein the plurality of first depressions each have an elliptical shape defined by bulbous ends, wherein the plurality of first depressions are arranged on the sheet material in offset parallel rows, wherein the bulbous ends of the plurality of first depressions in a first row are offset from the bulbous ends of the plurality of first depressions in an adjacent second row such that the bulbous ends of the plurality of first depressions in the first row are generally aligned with a midpoint of the plurality of first depressions in the adjacent second row, said first layer of material having a plurality of second depressions depending from said third plane toward said second plane, at least a portion of said plurality of second depressions terminating in or adjacent said second plane.

2. The three-dimensional sheet material of claim 1, wherein at least a portion of said plurality of first or second depressions define apertures therein.

3. The three-dimensional sheet material of claim 1, wherein at least a portion of said plurality of second depressions form liquid channels having a generally decreasing dimension as viewed in the direction from said first plane towards said second plane and which terminate in apertures to create liquid capillaries which permit liquid flow in the direction from said first plane towards said second plane.

4. The three-dimensional sheet material of claim 1, wherein at least a portion of said plurality of first depressions are uniformly spaced over at least a portion of said first layer of material.

5. The three-dimensional sheet material of claim 4, wherein at least a portion of said plurality of second depressions are uniformly spaced over at least a portion of said first layer of material.

6. The three-dimensional sheet material of claim 1, wherein said first layer of material has a basis weight of between about 8 grams per square meter and about 200 grams per square meter.

7. The three-dimensional sheet material of claim 1, wherein said first layer of material has a thickness of between about 0.1 millimeters and about 4 millimeters.

8. The three-dimensional sheet material of claim 1, wherein said first layer of material has an overall thickness between said first plane and said second plane of between about 0.3 millimeters and about 15 millimeters.

9. The three-dimensional sheet material of claim 1, wherein said first layer of material has an upper thickness between said first plane and said third plane of between about 0.05 millimeters and about 12 millimeters.

10. The three-dimensional sheet material of claim 1, wherein said first layer of material has a lower thickness between said third plane and said second plane of between about 0.25 millimeters and about 8 millimeters.

11. The three-dimensional sheet material of claim 1, wherein said first layer of material defines a total surface area and wherein said portion of said top surface of said first layer of material located in said first plane is between about 20 percent and about 70 percent of said total surface area of said first layer of material.

12. The three-dimensional sheet material of claim 1, wherein said first layer of material is a fibrous nonwoven web.

13. The three-dimensional sheet material of claim 1, wherein the portion of said first layer of material located in said first plane is more hydrophobic than another portion of said first layer of material not located in said first plane.

14. The three-dimensional sheet material of claim 1, wherein the plurality of second depressions are circular in shape.

* * * * *